US008202860B2

(12) United States Patent
Stendel et al.

(10) Patent No.: US 8,202,860 B2
(45) Date of Patent: *Jun. 19, 2012

(54) METHODS AND COMPOSITIONS FOR TREATING PRIMARY AND SECONDARY TUMORS OF THE CENTRAL NERVOUS SYSTEM (CNS)

(75) Inventors: Ruediger Stendel, Berlin (DE); Rolf W. Pfirrmann, Lucerne (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 258 days.

This patent is subject to a terminal disclaimer.

(21) Appl. No.: 12/608,748

(22) Filed: Oct. 29, 2009

(65) Prior Publication Data
US 2010/0048542 A1  Feb. 25, 2010

Related U.S. Application Data

(60) Continuation of application No. 10/424,102, filed on Apr. 28, 2003, now Pat. No. 7,638,511, which is a continuation of application No. 10/281,138, filed on Oct. 28, 2002, now Pat. No. 6,815,441, which is a division of application No. 09/583,902, filed on Jun. 1, 2000, now Pat. No. 6,479,481.

(60) Provisional application No. 60/182,200, filed on Feb. 14, 2000, provisional application No. 60/174,607, filed on Jan. 5, 2000, provisional application No. 60/167,681, filed on Nov. 29, 1999, provisional application No. 60/151,050, filed on Aug. 27, 1999, provisional application No. 60/137,421, filed on Jun. 4, 1999.

(51) Int. Cl.
*A61K 31/54* (2006.01)
(52) U.S. Cl. .................................................. 514/222.5
(58) Field of Classification Search .................. None
See application file for complete search history.

(56) References Cited

U.S. PATENT DOCUMENTS

| 4,626,536 | A | 12/1986 | Pfirrmann |
| 6,080,397 | A | 6/2000 | Pfirrmann |

FOREIGN PATENT DOCUMENTS

| CA | 2302720 A1 | 9/2000 |
| EP | 0 253 662 A1 | 1/1988 |
| EP | 1066830 A2 | 1/2001 |
| JP | 60-105618 A | 6/1985 |
| JP | 63-72626 A | 4/1988 |
| JP | 5-505615 A | 8/1993 |
| JP | 2000-300661 A | 10/2000 |
| JP | 2000-516196 A | 12/2000 |
| JP | 2001-10976 A | 1/2001 |
| WO | WO 91/13628 A1 | 9/1991 |
| WO | WO 92/00743 | 1/1992 |

OTHER PUBLICATIONS

Trebuchet et al. Chirurgie, Sep. 1998, vol. 123, No. 4, pp. 343-350 (Abstract attached).*
Chyun et al. Med. Pediatr. Oncol., 1980, vol. 8, No. 3, pp. 305-308 (Abstract attached).*
Japanese Office Action entitled "Preliminary Notice of Reasons for Rejection", Dec. 4, 2008, and English language translation, pp. 1-7.
Clarke, K. et al., KRN8602 (MX2-hydrochloride): an active new agent for the treatment of recurrent high-grade glioma, *J Clin Oncol* Aug. 1999; 17(8) 2579-84.
Jacobi, C.A. et al., Inhibition of Peritoneal Tumor Cell Growth and Implantation in Laparoscopic Surgery in a Rat Model, *Am J of Surgery*, 174, Sep. 1997, 359-363.
Jacobi, C.A. et al., Intraperitoneal installation of taurolidine and heparin for the prevention of intraperitoneal tumor growth and trocar metastases in laparoscopic surgery in a rat model, *Langenbecks Arch Chir* (1997) 382 [Suppl 1]: S31-S36.
Monson, J.R.T. et al., Abrogation of tumor necrosis factor (TNF) toxicity in the murine model by taurolidine: support for synergism of TNF with endotoxin, *Br. J. Surg.*, 77(6), Jun. 1990, A708.
Monson, J.R.T. et al., Preliminary evidence that taurolidine is anti-neoplastic as well as anti-endotoxin and anti-microbial, *Br. J. Surg.*, 77(6), Jun. 1990, A711.
Monson, J.R.T. et al., Taurolidine as an anti-neoplastic agent: a previously undiscovered role?, *Br. J. Surg.*, 77(12), Dec. 1990, 1432.
Monson, J.R.T., et al., Taurolidine inhibits tumour necrosis factor (TNF) toxicity—new evidence of TNF and endotoxin synergy, *Euro. J. Surg. Oncology* 1993; 19:226-231.

* cited by examiner

*Primary Examiner* — James D Anderson
(74) *Attorney, Agent, or Firm* — Rothwell, Figg, Ernst & Manbeck, P.C.

(57) ABSTRACT

Methods and compositions for the treatment and/or prophylaxis and/or suppression of primary and/or secondary tumors of the central nervous system (brain and spinal cord, eyes) in mammalian subjects are disclosed, wherein an effective dose of a methylol transfer agent such as Taurolidine and/or Taurultam and/or a bioequivalent is administered to a mammalian subject suffering from, or at risk of growth of, tumors of the central nervous system. Furthermore, methods for local application of Taurolidine and/or Taurultam and/or a bioequivalent in solution are disclosed using microdialysis methods, irrigation methods, implantion methods and angiographic methods.

12 Claims, No Drawings

METHODS AND COMPOSITIONS FOR TREATING PRIMARY AND SECONDARY TUMORS OF THE CENTRAL NERVOUS SYSTEM (CNS)

CROSS-RELATED REFERENCE TO RELATED APPLICATIONS

This application is a continuation of U.S. application Ser. No. 10/424,102, filed Apr. 28, 2003, now U.S. Pat. No. 7,638,511, which is a continuation of patented U.S. application Ser. No. 10/281,138, filed Oct. 28, 2002, now U.S. Pat. No. 6,815,441, which is a divisional of U.S. application Ser. No. 09/583,902, filed Jun. 1, 2000, now U.S. Pat. No. 6,479,481 B1, which claims the benefit of U.S. Provisional Application No. 60/137,421 filed Jun. 4, 1999, and which claims the benefit of U.S. Provisional Application No. 60/151,050 filed Aug. 27, 1999, and which claims the benefit of U.S. Provisional Application No. 60/167,681 filed Nov. 29, 1999, and which claims the benefit of U.S. Provisional Application No. 60/174,607, filed Jan. 5, 2000 and which claims the benefit of U.S. Provisional Application No. 60/182,200 filed Feb. 14, 2000.

BACKGROUND OF THE INVENTION

1. Field of the Invention

The present invention is in the field of treating tumors of the central nervous system (CNS).

2. Description of the Background Art

Taurolidine (Bis-(1,1-dioxoperhydro-1,2,4-thiadiazinyl-4)methane) was developed by Geistlich Pharma. It is a white crystalline substance, water soluble up to 2%. It is made up of two molecules of taurinamid and three molecules formaldehyde forming a two-ringed structure bridged by a methylene group.

Taurolidine has primarily an antibiotic and anti-endotoxin effect. It acts by a chemical reaction, so no microorganism resistance has been observed as yet. This effect of taurolidine is mediated by its active metabolites, which are donators of active methylol-groups: Methylol-Taurultam and Methylol-Taurinamide. The active methylol groups inactivate by reacting with the cell wall of bacteria and with the primary amino groups of endotoxins.

Additional effects of taurolidine were reported in the past: inhibition of TNF and IL-1Beta in mononuclear cells (Bedrosian 1991), inhibition of Tumor Necrosis Factor Toxicity, and inhibition of Peritoneal Tumor Cell Growth in Laparoscopic Surgery (Jacobi 1997).

Taurolidine solutions have been used as instillation or rinsing solutions of the abdominal cavity in cases of peritonitis. In post-operative instillations, conscious patients have reported as a side-effect irritation of the nerves of the peritoneum, and sometimes strong burning sensations which require intravenous administration of pain killers or anaesthesia. Monson et al. PCT International Publication Number WO 92/00743 discloses a selective direct inhibiting effect of Taurolidine and/or Taurultam on certain body tumors. (Monson J R T, Ramsey P S, Donohue J H. Preliminary evidence that taurolidine is anti-neoplastic as well as anti-endotoxin and anti-microbial. Abstract. Br J Surg 77(6) 1990, A711) on B16 melanoma cells and Meth A sarcoma cells in a mice model in vivo, and on fibroblastic tumor cells, LS174T (colon-) carcinoma cells and Jurkat (leukemic-) cells in vitro (International Patent PCT No. PCT/EP91/01269, International Publication Number WO 92/00743 PCT "Use of Taurolidine and/or Taurultam for the treatment of tumors"). However, primary tumors of the brain and medulla of the Central Nervous System (CNS) are very different from those of the body. Nerve cells differ significantly from cells of other organs, and have a much more complex construction. Nerve cells are characterized by a great number of branches which serve to transmit impulses and sensations, including dendrites for reception of impulses, and neurites or axons for emission of impulses. Neurogliae are glia-cells which are present in greater numbers than neurons, and render stability to the nerve cells. Glia-cells are responsible for metabolism and protection of sensitive nerve cells. The cells from which CNS tumors arise have a different metabolism as compared to other tumor cells. Metastases of CNS tumors outside the nervous system are very rare. Effective surgical treatment is often impossible since the tumors are located in functionally important areas, or spread diffusely.

Primary tumors of the brain and spinal cord arise from the different cell types of the CNS. These cell types are neurons, which are responsible for the neuronal function and the glial cells, which have supporting and nutritioning functions. According to the different subtypes of glial and neuronal cells, there are different types of CNS-tumors. The most common brain tumors arise from the glial cells. Various subtypes (astrozytoma, oligodendroglioma, ependymoma, etc.) are encompassed by the term "glioma".

Gliomas are the most common primary brain tumors. The incidence of gliomas is about 5/100,000 persons per year. More than 50% are glioblastoma, the most malignant form, which is responsible for more than 2.5% of the total tumor associated mortality. More than 95% of the patients die within 2 years following diagnosis despite aggressive therapy including surgery, radiotherapy and chemotherapy.

Brain tumors have some special characteristics as compared to "peripheral" tumors. They act as space occupying lesions, caused by the bony skull. This situation causes herniation and death when the tumor grows larger than can be accommodated. Furthermore, primary brain tumors often metastasize via the cerebrospinal fluid within the whole central nervous system. The brain tumor cells have a lower cohesion within the cell formation as compared to "peripheral" tumor cells (Jänisch W.: Pathologie der Geschwülste des Zentralnervensystems In: Klinische Neuropathologie, J. Cervós-Navarro and R. Ferszt (Eds.) Thieme, Stuttgart, N.Y., 1989). In addition, the metabolism of brain tumors are influenced by the blood/brain barrier.

Both types of tumors, glial and neuronal, can develop malignantly. Malignant gliomas are more frequent as compared to benign gliomas (85% vs. 15%). In the U.S. there are about 20,000 new glioma and medulloblastoma cases per year. The glioblastoma is most common (about 65% among astrocytoma).

Therapeutic options of primary CNS-tumors include surgery, radiotherapy and chemotherapy. Complete resection is often impossible because of poorly defined tumor borders and location within the brain area. Nearly all malignant glioma reoccur within months, 90% on the original site. Reoperation for a recurrent glioma typically extends survival by about 36 weeks (10 weeks with good quality of life). There is no well designed study regarding the beneficial effect of radiotherapy following glioma surgery. In patients older than 65 years, the median survival following tumor biopsy plus radiation is about 17 weeks, and following tumor removal plus radiation about 30 weeks (the peak incidence of glioblastoma is at an age of about 60 years). However, complete tumor removal plus radiotherapy is considered the reference standard in glioma therapy.

Chemotherapy using alkylating agents has a positive response rate of about 30%. A positive response generally extends the survival by 6-8 weeks. However, only about 50% of the patients treated with chemotherapy using alkylating agents are able to maintain regular activities.

Despite progress in diagnosis and treatment, the prognosis of patients with malignant primary CNS-tumors is still poor. The median survival of glioblastoma patients following optimal therapy including complete extirpation and radiation is less than about 10 months (about 1.6 years in grade III astrocytomas). The 1-year survival rate of patients with glioblastoma is about 35%, the 2-year survival rate about 8%.

Some primary malignant central nervous system tumors cannot be treated surgically because of their location or diffuse extension (gliomatosis, diffuse brain stem gliomas). Chemotherapy is not generally recommended, since the response rate on these alkylating agents (BCNU, CCNU, Procarbazine) is about 10% of patients (data from Greenberg M S. Handbook of Neurosurgery. Third edition 1994, Greenberg Graphics Inc., Lakeland, Fla., USA). Heretofore, no therapy could be offered to those patients despite a palliative radiation. Thus, the therapy of primary malignant tumors of the central nervous system has been very unsatisfactory.

There remains a need in the art for new methods and compositions for treating tumors of the central nervous system.

SUMMARY OF THE INVENTION

The present invention relates to the use of methoyl transfer agents, including Taurolidine and/or Taurultam, for the treatment of tumors of the central nervous system in mammals. Despite the irritation of the nerves of the peritoneum and strong burning sensations which have been side-effects of peritonitis post-operative instillations of Taurolidine, it surprisingly has been found that CNS nerve cells, including the particularly sensitive stem cells of embryo meningeal cells, remain unaffected following administration of Taurolidine/Taurultam solutions.

It was surprising to demonstrate a direct antineoplastic effect of Taurolidine and/or Taurultam on neuronal and glial tumor cell lines. This effect was very unexpected due to the quite different behavior of brain tumor cells as compared to other tumor cells, particularly concerning their response to chemotherapeutic agents. Furthermore, the antineoplastic effect of Taurolidine and/or Taurultam was thought only to be associated with the influence on cell adhesion molecules, which explains the prevention of metastatic tumor growth following endoscopic abdominal tumor surgery. A direct antineoplastic effect on brain tumor cells was very unexpected.

DETAILED DESCRIPTION OF THE INVENTION

Taurolidine and Taurultam, its intermediate and active metabolite, are methylol transfer agents. They act by transferring methylol groups at the site of action. Both substances have low toxicity and are not cytotoxic against normal cells.

This invention provides for treatment and/or prophylaxis of tumors and/or suppressing of primary and secondary tumors of the central nervous system in mammalian subjects wherein an effective dose of a methylol transfer agent such as Taurolidine and/or Taurultam is administered to a mammalian subject suffering from or at risk of central nervous system tumor growth. Furthermore the invention includes special methods for local application of Taurolidine and/or Taurultam in solution using microdialysis methods, irrigation methods, implantation methods, and angiographic methods. The terms Taurolidine and/or Taurultam as used herein are intended to refer to the compounds Taurolidine, Taurultam, Taurultam-glucose (as described below), and their substantial bioequivalents or agents which act in a substantially similar manner. For example, an aminoglycan derived from Taurultam and any other suitable derivate of Taurolidine and/or Taurultam, or agents which act in a substantially similar manner, can be utilized like Taurolidine and/or Taurultam according to the invention.

The term "treatment" as used herein is intended to refer to treatment, prophylaxis and/or suppression of CNS tumors. The present invention is applicable to treatment of CNS tumors, which may include:

Glioblastoma Multiforme (GBM)
High grade gliomas
Anaplastic oligodendroglioma
Low grade gliomas
Recurrent malignant gliomas
Anaplastic astrocytoma
Advanced metastatic melanoma
Recurrent high grade primary brain tumors
Primary central nervous system lymphoma
Leptomeningeal dissemination of malignant glioma (meningeal gliomatosis).

Treatment takes place primarily in connection with surgical intervention, such as surgical removal of a CNS tumor, as well as postoperative local application of taurolidine and/or Taurultam solution while using, for example, a microdialysis method or an irrigation method. Since the blood/brain barrier is passed by Taurolidine and/or Taurultam, it also may be appropriate to administer 2% taurolidine solutions or 3% Taurultam solutions intravenously through a central catheter. Here, in addition to the antineoplastic action, prevention of infection is also of great advantage for the patient. In this connection, dosage appropriately may be 15-20 g of taurolidine as a 2% solution through a central catheter daily for 7-8 days, or alternatively as 3% Taurultam solution, 20-30 g Taurultam daily, for 7-8 days with adults. This is intended to preserve or improve neurological function and health-related quality of life. For local application in connection with operations in the brain, glucose-based solutions, with or without electrolytes, and which additionally contain 0.2-1% Taurolidine, Taurultam or Taurultam-glucose, are preferred.

Basic treatment solutions preferably are modeled after cerebrospinal solution, contain glucose and electrolytes, are substantially isotonic to the extent possible and have a slightly alkaline pH value of about 7.3-7.35. The following ingredients may be included in a basic solution:

Bicarbonate
Sodium
Potassium
Calcium
Magnesium
Lactate
Chloride
Glucose

Taurolidine, Taurultam, Taurultam-glucose or the like are added to a basic solution.

Exemplary Basic Solution

A basic solution may, for example, be comprised of Cerebrospinal Fluid (CSF) components as shown in the following table.

| CONSTITUENT | UNITS | CSF | PLASMA | CSF:plasma ratio |
|---|---|---|---|---|
| osmolarity | mOsm/L | 295 | 295 | 1.0 |
| $H_2O$ content | | 99% | 93% | |

| CONSTITUENT | UNITS | CSF | PLASMA | CSF:plasma ratio |
|---|---|---|---|---|
| sodium | mEq/L | 138 | 138 | 1.0 |
| potassium | mEq/L | 2.8 | 4.5 | 0.6 |
| chloride | mEq/L | 119 | 102 | 1.2 |
| calcium | mEq/L | 2.1 | 4.8 | 0.4 |
| $pCO_2$ | mm HG | 47 | 41 | 1.1 |
| pH | | 7.33 | 7.41 | |
| $pO_2$ | mm Hg | 43 | 104 | 0.4 |
| glucose | mg/dl | 60 | 90 | 0.67 |
| lactate | mEq/L | 1.6 | 1.0 | 1.6 |

Exemplary Amino-Sugar/Taurultam-Glucose Treatment Agent 13.6 g Taurultam and 18 g of anhydrous glucose were weighed out into a 250 ml serum bottle, and 200 ml of distilled water were added. The solution obtained was heated to 100° C. for 30 minutes. The clear solution was evaporated in a vacuum until dry. The residue was absorbed in 96% alcohol and placed in an Erlenmeyer flask overnight for forming crystals.

Amino-sugar/Taurultam-glucose crystallized out, and the crystals were suction filtered with a raw yield of 5.3 g.

From alcohol mixed with a few drops of water, white crystals were recrystallized:

Melting point: 168°-170° C.

Calculated: C=36.23 H=6.03 N=9.39 S=10.74%

Found: C=36.26 H=6.10 N=9.09 S=10.90%

The IR spectrum corresponded NMR in $DMSO_6$ 200 MHZ. Sulfonamide NH coupling to its adjacent $CH_2$, one OH coupling to $CH_2$ and three OH's couplings to CH indicated internal loss of water and that the chain had cyclised to form a sugar.

Solutions for Use in the Irrigation and/or Microdialysis Methods

| Solution 1 | 1000 ml contain: |
|---|---|
| Glucose monohydrate for injection purposes | 27.500 g |
| Sodium | 3.382 g |
| Potassium | 0.157 g |
| $Ca^{++}$ | 0.009 g |
| $Cl^-$ | 5.520 g |
| Taurultam | 0.5% |

The solution is slightly hypertonic.
The glucose can be replaced by 25 g levulose (fructose).
The solution is then insulin-independent.

| Solution 2 | 1000 ml contain: |
|---|---|
| Sodium | 3.151 g |
| Potassium | 0.156 g |
| $Ca^{++}$ | 0.066 g |
| $Mg^{++}$ | 0.033 g |
| $Cl^-$ | 3.900 g |
| Acetate | 2.173 g |
| Taurultam-glucose | 0.5% |

The pH value is set at pH 7.3.

The solutions 1 and 2 are filtered in an appropriately sterile manner with a 0.1 micron sterile filter and aseptically deposited in sterile infusion bottles.

| Solution 3 | 1000 ml contain |
|---|---|
| Glucose monohydrate for injection purposes | 18.330 g |
| Sodium lactate | 2.460 g |
| Sodium chloride | 2.800 g |
| Potassium chloride | 0.187 g |
| Calcium chloride $2H_2O$ | 0.147 g |
| Magnesium chloride $6H_2O$ | 0.152 g |
| Taurolidine | 1% |

The pH is set at 7.3. The solution is filtered in a sterile manner and aseptically deposited in 100 ml infusion bottles.

| Solution 4 | 1000 ml contain: |
|---|---|
| Sodium chloride | 4.000 g |
| Potassium chloride | 0.050 g |
| Calcium chloride $2H_2O$ | 0.066 g |
| Sodium hydrogen carbonate | 0.050 g |
| Taurultam | 1% |

The solution is set at a pH of 7.5 prior to sterilization and subsequently filtered in a sterile manner, deposited in 250 ml infusion bottles and sterilized with steam for 15 minutes at 121° C.

Exemplary Treatment Modalities

Taurolidine and/or Taurultam may be administered by injection or infusion, or by local application. Isotonic glucose solution and/or artificial cerebrospinal fluid solution as described above may be used containing Taurolidine and/or Taurultam, or a substantial bioequivalent thereof. The local administration can be performed via (a) microdialysis using a probe tube, and (b) direct irrigation and/or implantation of a catheter, and single or repeated irrigation. A Microdialysis-method can be utilized in nonextirpated tumors or reoccurrences as well as in inoperable tumors, e.g., diffuse brain stem gliomas. An irrigation/catheter method may be utilized following complete or incomplete tumor extirpation.

a) Microdialysis Method

An isotonic solution as described above, is stored at body temperature in a tank. A small pump (subcutaneous or outside the body) forces the Taurolidine and/or Taurultam solution via tubular microprobe to the tumor and/or its surrounding. The microprobe may be formed of plastic material with a small lumen. The tip of the probe may have a semipermeable membrane so that an osmotic fluid exchange can occur. In this way, the Taurolidine and/or Taurultam can diffuse inside the tumor and its surroundings. Different types of probes can include a probe with a small tip to terminate directly inside the tumor. With large tumors, a large membrane can be provided at the end of the probe to lie inside the tumor cavity or on the surface of the tumor. In some cases with large tumors, it may be necessary to implant more than one probe.

b) Irrigation/Catheter Method

Following removal of a tumor, or with cystic tumors, direct single or repeated irrigation of the tumor cavity or area may be performed. Furthermore, a catheter can be implanted in the tumor cavity for repeated local administration with Taurolidine and/or Taurultam.

c) Angiographic Method

Another method for regional application of Taurolidine and/or Taurultam may be provided for tumors with blood supply by one or a few dominant feeder arteries. Taurolidine and/or Taurultam may be administered by an angiographic catheter, which may be introduced supraselectively into the feeders. The Taurolidine and/or Taurultam then may be administered once or repeatedly.

d) Implantion Method

Following complete or incomplete removal of a tumor, direct single or repeated implantion of a matrix containing Taurolidine and/or Taurultam into the tumor cavity may be performed.

Results

Taurolidine and/or Taurultam have been found to inhibit directly the growth of CNS tumor cell lines, including neuronal (HT22) as well as glial (C6) tumor cell lines. Furthermore, this action was shown to be selective in that the growth of primary cell lines of a fetal rat central nervous system required significantly higher concentrations and a significantly longer contact time for inhibition, as compared to tumor cells (taking into account a very high general sensitivity of primary cell lines of the fetal rat central nervous system). The effect was concentration-dependent. Antineoplastic effects of concentrations of 0.1 to 4 mg/ml Taurolidine and/or Taurultam in PVP and glucose solution was demonstrated. The tumor cells were inhibited starting after 10 minutes. Following about 1 to 2 hours 90% of the tumor cells were inhibited.

Summary

The tumor-inhibiting agents of the present invention, including Taurolidine and/or Taurultam, may be administered by injection or infusion. Agents in accordance with the present invention may be administered locally using microdialysis utilizing probes, as well as regionally using superselective angiographic catheters with continuous or sequential administration of an agent in accordance with the present invention.

Probes for practicing a microdialysis method in accordance with the invention can be placed using neuronavigation, MRI guidance and/or ultrasound guidance. A diagnostic biopsy can be taken from the tumor to make a histological diagnosis during the same surgical procedure in which treatment utilizing a microdialysis method in accordance with the invention is utilized. Alternatively, during a microdialysis method in accordance with the present invention, fluid can be obtained from the tumor or its surroundings so as to maintain a desired fluid level in the area of the tumor.

An agent in accordance with the present invention can be administered by a permanently or temporarily implanted catheter for continuous or repeated local irrigation of a tumor or its surroundings. The treatment agent can be administered locally by irrigation of the surroundings of a totally or partially extirpated tumor.

In preferred embodiments, Taurolidine and/or Taurultam is administered intravenously in a dosage range of about 50-500 mg/kg per day, sequentially or by continuous administration.

Separately or simultaneously with administration of a methylol transfer agent in accordance with the present invention, other agents can be administered to the patient, including cytotoxic, antineoplastic agents (including alkylating agents, and/or agents involved in tumor metabolism). Alternatively or additionally, if desired, other tumor treating agents may be administered, such as interleukin-1, interleukin-2, interferon, or other immunomodulating agents.

The advantages of combination therapy include:

1) Synergic effects may be realized from employment of a combination therapy with regard to achievement of tumor control and survival improvement.

2) Dosage reduction in administration of antineoplastic medicaments will lead to amelioration of the considerable side effects, such as hair loss, nausea, vomiting, diarrhea, etc.

3) Combination therapy allows for different ways of application of the medicaments, e.g., local Taurolidine/Taurultam administration, systemic general chemotherapy, etc.

Taurolidine and/or Taurultam can be administered by intraperitoneal application in combination with local inthratecal or intravenous general chemotherapy.

This combined administration facilitates prevention of development of metastates and dissemination thereof into the liquor and into the brain during laparotomy or laparoscopic tumor surgery.

Example 1

Taurolidine and Taurultam have been found to inhibit directly the growth of neuronal (HT22, mouse), glial (C6, rat), and mixed neuronal and glial (U373, human) tumor cell lines. For the latter cell line, however, the experiments are not complete as yet. Furthermore, this action was shown to be selective in that the growth of normal central nervous system cells was not significantly inhibited. The effect was concentration-dependent. Antineoplastic effects of concentrations of 0.1 to 4 mg/ml Taurolidine and/or Taurultam was demonstrated. The tumor cells were inhibited selectively beginning after 30 minutes. Following 1 to 3 hours about 90% of the tumor cells were inhibited. For the cell culture, cells were used in RPM1 1640 medium and plated in Falcon flasks. Following incubation with 0.1-4 mg/ml Taurolidine and Taurultam, cytological changes were recorded after 10, 30, 60, 120, 180, 300 minutes, and after 24 and 48 hours.

Beginning following 30 minutes, cytological changes were observed, including: (a) development of vacuoles, and (b) condensation of nuclei, shrinking of cytoplasm, and cell death.

Ultrastructural changes include: swelling of mitochondria, swelling of nuclei, swelling of cytoplasm, and rupture of cell membrane. The first changes occurred after 10 minutes, increasing with time and concentration.

The results of DNA-FACS supported the cytological and ultrastructural observations.

The effect of taurolidine/taurultam on primary CNS-cells was investigated using the brain cells of rat fetuses in a cell culture. We found no significant cytological effect following 48 hours.

For treatment of glioma patients, Taurolidine and/or Taurultam may be administered by injection or infusion, or by local application. The local administration can be performed via (a) microdialysis using tubular probes, and (b) direct irrigation and/or implantation of a temporary or permanent catheter, and single or repeated irrigation.

The Microdialysis-method can be utilized in nonextirpated tumors or reoccurrences as well as in inoperable tumors, e.g., diffuse brain stem gliomas. The irrigation/catheter method may be utilize following complete or incomplete tumor extirpation.

Example 2

Combined Therapy with Taurolidine and Additionally Antineoplasatic Agents in Patients with Glioblastoma, Gliosarcoma, Anaplasatic Glioma and Astrocytoma The combination of Taurolidine/Taurultam with antineoplastic agents for treatment of brain tumors such as glioblastoma, astrocytoma and gliosarcoma offers a number of advantages.

The combination of, for example, alkylated agents and Taurolidine and/or Taurultam avoids or reduces side effects such as nausea, vomiting, diarrhea, etc., induced by use of antineoplastic medicaments. The dosage of these antineoplastic medicaments can be reduced by up to half or more and still increase the overall response rate (disease stabilization rate) by synergic effects.

Radiotherapy with its strong side effects can also be avoided or reduced in many cases.

The recurrency rate of dissemination of tumors in primary brain tumors in glioblastoma miltiforma and astrocytoma can also be reduced by a combined therapy.

Of various antineoplastic agents, those medicaments should be chosen which, due to their molecular structure, are unlikely to interact with Taurolidine and/or Taurultam. It is also preferable to direct the combined chemotherapy at the tumor in different ways, e.g., locally to the brain tumor via direct irrigation of Taurolidine and/or Taurultam, or by implantation of a permanent catheter, or via microcialysis in using tubes, and by established chemotherapy i.v. or orally, e.g. by administration of Temozolamide 100 mg/m² once daily for 5 days.

Alternatively, after surgical resection of glioblastoma, localized and sustained delivery of 5-fluorouracil (f-FU) can be provided in combination with Taurolidine and/or Taurultam via central catheter as drop infusion for several days.

In cases of laparoscopic emergency surgery of tumors, laparoscopic cholecystectomy, cholecystitis, laparoscopic cholorectal surgery, etc. in tumor patients as well as in general laparotomy, the intraperitoneal administration of 2% Taurolidine as lavage or instillation in combination with regular i.v. chemotherapy for combating tumors, prevention of metastases and dissemination in the brain, is possible.

In leptomeningeal dissemination of malignant glioma (meningeal gliomatosis) associated with poor survival intrathecal (IT) chemotherapeutic agents used in combination with local or systemic administration of Taurolidine and/or Taurultam solutions to achieve tumor control and improve survival, may be helpful.

The following antineoplastic agents may be compatible for combination with Taurolidine and/or Tarultam:

| | | |
|---|---|---|
| PCV-Chemotherapy: | Combination of: | procarbazine HCl lomustine (CCNU) (CeeNu) vincristine sulfate |
| Cisplatin | | |
| Methotrexate | | |
| Cytosinarabinoside (ara-C) | cytarabline hydrochlorid | |
| Temozolamide | | |
| MX2-hydrochloride | | |
| Topocetan | | |
| Paclitaxel (Taxol) | | |
| Interleukin-2 (IL-2) | in simultaneous administration of Interleukin-1 (IL-1) and lymphokine-activated killer-cell or TNF, a combination with Taurolidine leads to reduction of toxicity of the cytokines and is more agreeable to the patient. | |

The nitrosourea medicaments such as ACNU/BCNU/CCNU are generally applied in lower concentration, e.g., 30-50 mg/m² i.v. once per week of 6 weeks. Temozolamide is given orally in a dosage of 50-100 mg/m² for 5 days. MX-2-hydrochlorid is given as antra venous bolus at 20 mg/m² every 28th day for several months until progression occurs.

As another choice, further antineoplastic medicaments are suitable for combination:

| | |
|---|---|
| Cyclophospamid | approximately 150 mg/m² |
| Fluorouracil (5-FU) | 40 mg/m² as local bolus or in the form of micropheres as intrathecal (IT)-chemotherapy |
| Doxorubicin | 10-15 mg/m² i.v. |
| Hydroxycarbamide | |

Cytosinarabinosides (ara-C), thiotriethylene-phosphoramide (thio-TEPA), and Neocarzinostatis can be administered in low doses in IT-chemotherapy in various combinations with Taurolidine and/or Taurultam for improvement of survival and achievement of tumor control and prevention of dissemination, respectively.

Dosage

The solution for delivery to a patient should contain an effective dosage of Taurolidine and/or Taurultam and/or Taurultam-glucose in the tissue-culture of glioblastoma multiform-tumor cells: as little as 0.1-4 mg/ml Taurolidine inhibits or kills tumor cells in tissue-culture.

Taurultam so far has been shown to be almost twice as effective as Taurolidine, the explanation of which may be found in the equilibrium of Taurolidine in aqueous solution between Methylol-Taurultam and Taurultam.

Taurultam-glucose, on the other hand, has to be dosaged about twice as high as Taurultam, as the molecular weight from Taurultam increases from 136 to 298.

When administered to patients utilizing the irrigation/catheter method described above, a concentration of at least about 4 mg/ml Taurolidine, Taurultam or Taurultam-glucose, respectively, should be utilized.

The invention claimed is:

1. A method of inhibiting growth of a tumor in a central nervous system (CNS) of a mammal, comprising surgically removing a CNS tumor from a CNS tumor site, and administering to said mammal a methylol transfer agent comprising taurolidine, taurultam, a combination of taurolidine and taurultam, methylol taurinamide, methylol-taurultam, an aminoglycan of taurultam, or taurultam-glucose, wherein said methylol transfer agent is administered locally to said CNS tumor site after surgically removing said CNS tumor, in a combination therapy in which said methylol transfer agent also is administered to said mammal intravenously.

2. The method of claim 1, wherein said methylol transfer agent comprises taurolidine, taurultam or a combination thereof.

3. The method of claim 1, wherein said tumor is a glioma.

4. The method of claim 1, wherein said tumor is a neuroblastoma.

5. The method of claim 1, wherein said tumor is an astrocytoma.

6. The method of claim 1, wherein said tumor is meningeal.

7. The method of claim 1, wherein said tumor is a CNS lymphoma.

8. A method of inhibiting metastases and dissemination of a tumor in a central nervous system (CNS) of a mammal, wherein said tumor is derived from a non-CNS primary tumor removed from a tumor site in the mammal during tumor surgery, the method comprising surgically removing the tumor from said tumor site, and administering to said mammal a methylol transfer agent comprising taurolidine, taurultam, a combination of taurolidine and taurultam, methylol taurinamide, methylol-taurultam, an aminoglycan of taurultam, or taurultam-glucose, wherein said methylol transfer agent is administered locally to said tumor site after surgically removing said tumor, in a combination therapy in which said methylol transfer agent also is administered to said mammal intravenously, wherein said mammal is a CNS tumor patient.

9. The method of claim 8, wherein said methylol transfer agent comprises taurolidine, taurultam or a combination thereof.

10. The method of claim 8 wherein said surgery is laparotomy or laparoscopic tumor surgery.

11. The method of claim 1, further comprising administering an alkylating agent.

12. The method of claim 8, further comprising administering an alkylating agent.

* * * * *